United States Patent [19]
Jenkins, Jr.

[11] Patent Number: 5,722,978
[45] Date of Patent: *Mar. 3, 1998

[54] OSTEOTOMY SYSTEM

[76] Inventor: Joseph Robert Jenkins, Jr., 12203 Becontree Dr., Baton Rouge, La. 70810

[*] Notice: The term of this patent shall not extend beyond the expiration date of Pat. No. 5,613,969.

[21] Appl. No.: 615,716

[22] Filed: Mar. 13, 1996

[51] Int. Cl.⁶ .................................................. A61B 17/15
[52] U.S. Cl. ........................ 606/87; 606/86; 606/88; 606/79; 606/82; 606/96
[58] Field of Search .......................... 606/86, 87, 88, 606/79, 82, 96

[56] References Cited

U.S. PATENT DOCUMENTS

| | | |
|---|---|---|
| 2,570,465 | 10/1951 | Lundholm . |
| 4,421,112 | 12/1983 | Mains et al. . |
| 4,952,213 | 8/1990 | Bowman et al. ............... 606/79 |
| 5,021,056 | 6/1991 | Hofmann et al. ............... 606/86 |
| 5,053,039 | 10/1991 | Hofmann et al. ............... 606/87 |
| 5,246,444 | 9/1993 | Schreiber ....................... 606/87 |
| 5,405,349 | 4/1995 | Burkinshaw et al. .......... 606/82 |

FOREIGN PATENT DOCUMENTS 194014A 9/1986 European Pat. Off. ........ 606/82

*Primary Examiner*—Michael Buiz
*Assistant Examiner*—Daphna Shai
*Attorney, Agent, or Firm*—Warner J. Delaune

[57] ABSTRACT

An osteotomy guide and surgical kit for performing a tibial osteotomy are provided, wherein the osteotomy guide comprises two or more rows of guide holes formed therethrough for attaching the guide onto a pair of guide pins in a predetermined relation to a tibia; a transverse slot, defining a transverse cutting plane; and a plurality of oblique slots angularly offset from the transverse slot, each oblique slot defining an oblique cutting plane. Additional features of the surgical kit include a transverse member adapted to pass through the transverse slot, which can be either a modified saw blade or a separate removable plate, and a locking device on the osteotomy guide for lockably engaging the transverse member and positioning the osteotomy guide at a predetermined location relative to the transverse member. A measurement guide hole is also provided in the same plane as the transverse slot so that accurate measurement of the tibial depth can be accomplished. At least two fixation holes are formed through the osteotomy guide in directions which are non-parallel to the guide holes so that additional fixation pins may be placed into the tibia for more stable positioning of the osteotomy guide. An alternative embodiment of the osteotomy guide is also provided which includes a removable clamp to lock the guide onto the guide pins prior to making the oblique cut. Methods of performing an osteotomy using the preferred and alternate embodiments of the osteotomy guide are also provided.

27 Claims, 7 Drawing Sheets

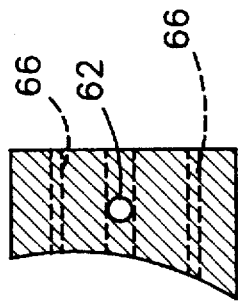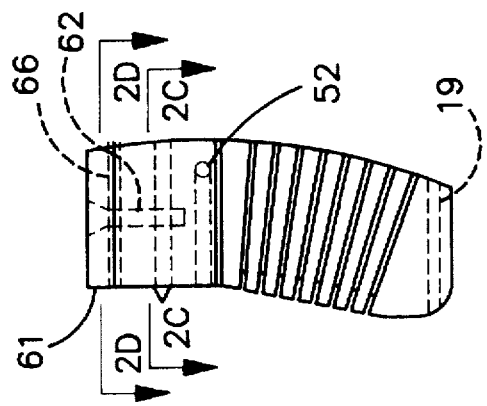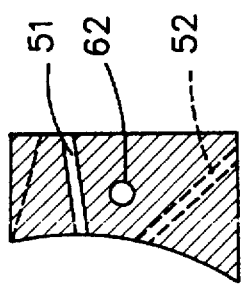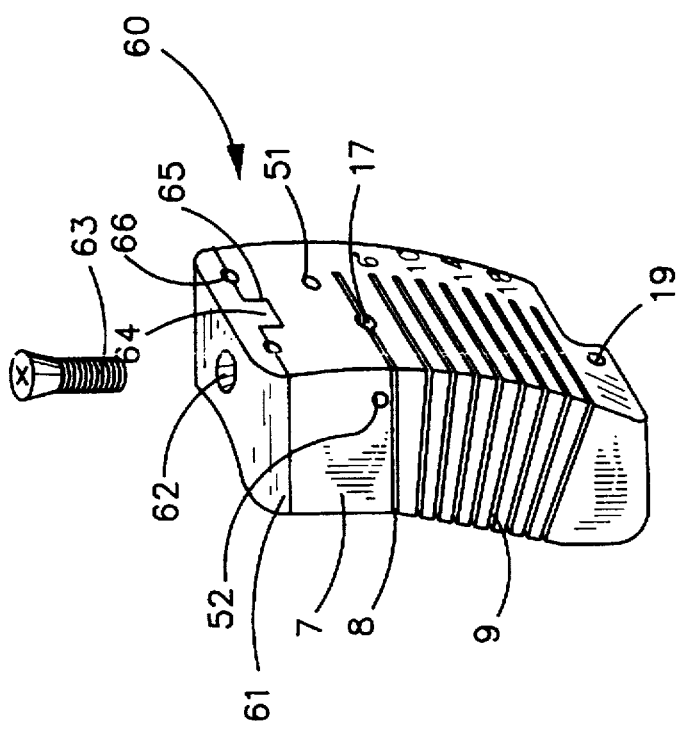

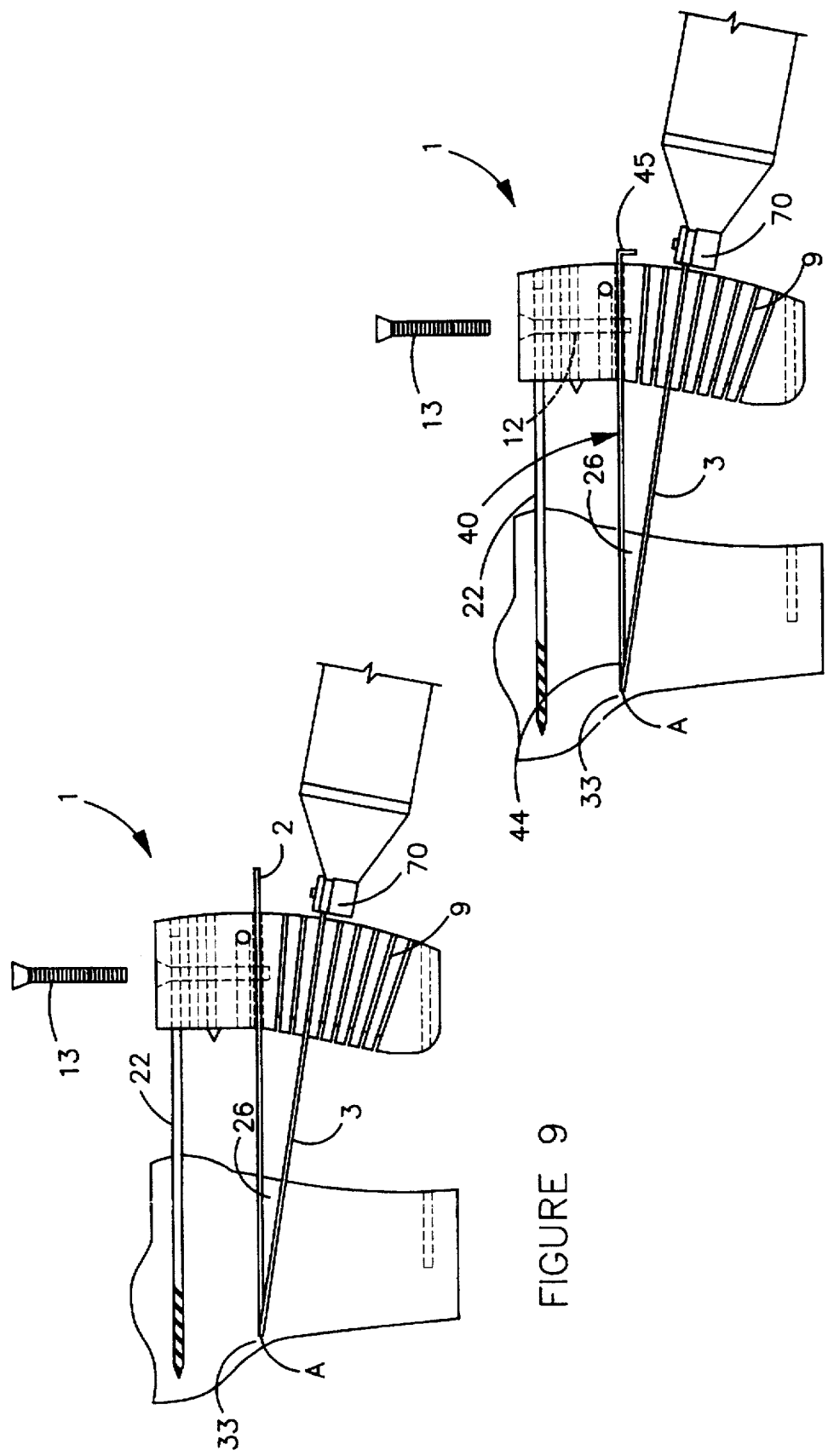

OSTEOTOMY SYSTEM

BACKGROUND OF THE INVENTION

I. Field of the Invention

The present invention relates generally to devices and methods for removing bone, and more particularly to such devices and methods used in performing osteotomies in humans.

II. Description of Prior Art

Many devices have been developed over the years to facilitate the removal of bone from the leg in order to correct certain malalignments of the legs. Malalignment of the anatomical axis and the mechanical axis along the tibia and femur in the coronal plane can lead to degenerative osteoarthritis of the knee. The abnormal loading stresses caused by such malalignment can be quite painful, and corrective surgery is often required to place the anatomical axes of the tibia and femur in proper alignment. The most common surgical procedure employed to correct tibiofemoral malalignment is the upper tibial osteotomy, which removes a wedge-shaped portion from the cancellous bone of the metaphysis of the tibia. The size of the wedge to be removed is determined by the surgeon upon an analysis of the gait of the patient, the degree of tibiofemoral malalignment, the patient's indication of the precise location of pain, and several other factors. After the wedge is removed, the head and distal portions of the tibia are slowly pulled toward one another to close the resultant gap. When the gap is closed, a plate or bracket device is used to keep the internal bone surfaces together until the surgical wound is properly healed. Because the tibia and femur are now in proper alignment, further degeneration of the knee joint is arrested and pain is reduced.

One such method and apparatus for performing tibial osteotomies is disclosed in U.S. Pat. Nos. 5,021,056 and 5,053,039, both issued to Hofmann, et al. The apparatus comprises, in part, a first guide assembly which grips the medial and lateral surfaces of the knee and serves to guide a saw blade in making the horizontal, or transverse, cut in the wedge. The first guide assembly is stabilized against the knee by at least two pins placed through the first guide assembly and into the head of the tibia. With the first guide assembly in place, a third hole in the first guide assembly is used to guide a drill bit completely through the head of the tibia adjacent to the location of the transverse cut. A depth gauge is then used to determine the width of the bone for the transverse cut. Below the stabilizing pins and the measurement hole, the first guide assembly includes a slot through which the saw blade must pass to make the transverse cut from the lateral side of the knee. Rather than cutting completely through the tibia head, however, the transverse cut is made such that an 8–10 millimeter bridge of cancellous bone is left on the medial side to act as a hinge during closure. The saw blade is then withdrawn from the transverse cut.

A second guide assembly is then placed at the site to provide guidance for the second, or oblique, cut. The second guide assembly includes a blade-shaped extension which is inserted into the transverse cut, and the guide is stabilized by the same two pins used for the first guide assembly. A plurality of oblique slots are formed into the second guide assembly which correspond to various angles for the oblique cut. The oblique slots are formed such that the end of the saw blade will meet with the end of the transverse cut previously made, thus enabling the cutting and removal of a wedge-shaped portion of bone from the tibia. After the wedge has been removed, the second guide assembly is removed from the osteotomy site.

To close the gap created by the removal of the wedge, an L-shaped plate is placed over the guide pins and across the portions of bone to be drawn together. The two guide pins are then removed and replaced by a pair of cancellous screws to hold the upper section of the plate against the bone surface. Next, a hole is drilled into the lateral tibia below the gap so that a ratcheted compression device can be employed to close the gap through plastic deformation of the medial bridge. One jaw of the compression device includes a rod which is inserted into the hole, while the other jaw includes a hook which engages the L-shaped plate. After the gap is closed, the compression device is removed, and additional cancellous screws are used to firmly attach the plate across the surgical wound.

While the Hofmann apparatus and method do appear to provide favorable results, there are several aspects to both the surgical procedure and the design of the components which allow the introduction of human error. For example, when the first guide assembly is placed across the knee, there is no way for the surgeon to obtain fluoroscopy images of the transverse cut and/or the pins. It may be possible for the first guide assembly to be constructed of a radiolucent material, but it would be more advantageous to dispense with this device in its entirety.

Second, after the transverse cut is made, the saw blade is withdrawn from the cut so that the transverse guide can be removed and the blade-shaped portion of the second guide assembly may be inserted. This movement of the tibia will necessarily cause deformation of the medial bridge and can sometimes cause it to fracture. If the medial bridge is completely fractured, an additional plate may be required to keep the bones together, leading to significant healing complications and a possibility of loss of correction. Ideally, the tibial osteotomy should be performed with a one-piece instrument that eliminates these concerns.

Third, once the wedge of bone has been removed, the guide pins are taken out of the tibia and replaced by cancellous screws to hold the L-shaped plate. While this procedure does not ordinarily cause problems, the screws may not accurately follow the hole left by the drill bit or the pins. In some instances, the screws may deviate away from the hole and push through the upper surface of the tibia head, because the operation is performed very close to the knee joint. Optimally, the screws which hold the plate to the tibia should use the drill bits or pins as a guide to verify that they will not harm other areas of the tibia.

One device, and its accompanying method of use, which resolves these problems is described in my previous U.S. application Ser. No. 08/384,856, now issued as U.S. Pat. No. 5,613,969, the disclosure of which is incorporated herein by reference. That device eliminates the need for a separate transverse cutting guide, because the transverse cut and the oblique cut are made using a single osteotomy guide. After the transverse cut is made, the motorized saw handle is removed from the transverse blade, and the transverse blade is left within the tibia. The guide is then slidably moved along the guide pins until it is locked onto the transverse blade a fixed distance away from the tibia. In the locked position, the guide allows for the oblique blade to meet the tip of the transverse blade precisely at the precalculated apex of the bone wedge.

While my previous invention offers features and advantages which have not heretofore been available in this field,

3 a number of additional or alternative features would also be beneficial. For example, such an invention would be more versatile if a single osteotomy guide could be used on a wide variety of tibia shapes and sizes, as well as for other common osteotomies such as distal and femoral proximal osteotomies. Furthermore, there may be instances where pin fixation is desired to lock the horizontal position of the guide relative to the tibia prior to making the oblique cut, either in addition to the locking of the guide onto the transverse blade, or as an alternative thereto. Finally, it would be advantageous to include a means for locking the osteotomy guide directly to the guide pins. Such a feature would permit the transverse blade to be removed after the transverse cut, and it would still provide precise alignment between the transverse cut and the oblique cut.

SUMMARY OF THE INVENTION

It is therefore an object of this invention to provide an improved tibial osteotomy system that allows greater use of fluoroscopy imaging during surgery.

Another object of this invention is to provide an improved tibial osteotomy system that reduces trauma to the tibial bone tissue during surgery.

It is also an object of this invention to provide an improved tibial osteotomy system that uses a minimum of surgical instruments.

It is a further object of this invention to provide an improved tibial osteotomy system that minimizes the risks of fracturing the roedial bridge.

Yet another object of this invention is to provide an improved tibial osteotomy system that is less sensitive to human error, and that reduces the possibility of misalignment of the instruments and fastening hardware.

Another object of this invention is to provide an improved tibial osteotomy system that can be used on a wide variety of tibia shapes and sizes.

Still another object of this invention is to provide an improved tibial osteotomy system that allows osteotomies to be performed more quickly than the prior art.

These and other objects and advantages of the present invention will no doubt become apparent to those skilled in the art after having read the following description of the preferred embodiment which are contained in and illustrated by the various drawing figures.

Therefore, in a preferred embodiment, an osteotomy guide and surgical kit for performing a tibial osteotomy are provided, wherein the osteotomy guide comprises two or more rows of guide holes formed therethrough for attaching the guide onto a pair of guide pins in a predetermined relation to a tibia; a transverse slot, defining a transverse cutting plane, adapted to receive and guide a transverse cutting blade for making a transverse cut into the tibia; and a plurality of oblique slots angularly offset from the transverse slot, each oblique slot defining an oblique cutting plane, adapted to receive and guide an oblique cutting blade for making a selected oblique cut into the tibia, wherein the intersection of each of the oblique cutting planes with the transverse cutting plane is adapted to define a wedge of bone which may be removed from the tibia. Additional features of the surgical kit include a transverse member adapted to pass through the transverse slot, which can be either a modified saw blade or a separate removable plate, and locking means on the osteotomy guide for lockably engaging the transverse member and positioning the osteotomy guide at a predetermined location relative to the transverse member. A measurement guide hole is also provided in the same plane as the transverse slot so that accurate measurement of the tibial depth can be accomplished. At least two fixation holes are formed through the osteotomy guide in directions which are non-parallel to the guide holes so that additional fixation pins may be placed into the tibia for more stable positioning of the osteotomy guide.

An alternative embodiment of the osteotomy guide is also provided which enables the guide to be locked onto the guide pins prior to making the oblique cut. This is accomplished by a removable clamp which can be screw-tightened into the body of the osteotomy guide to firmly grip the guide pins. Methods of performing an osteotomy using the preferred and alternate embodiments of the osteotomy guide are also provided.

BRIEF DESCRIPTION OF THE DRAWINGS

FIG. 2A is a perspective view of an alternative embodiment of the invention.

FIG. 2B is a side elevation view of the osteotomy guide of FIG. 2A.

FIG. 2C is a top sectional view of the osteotomy guide of FIG. 2A depicting the angular fixation pin holes.

FIG. 2D is a top sectional view of the osteotomy guide of FIG. 2A depicting the parallel fixation pin holes.

FIG. 9 is an elevation view of the osteotomy guide of FIG. 1B and the steps of locking the osteotomy guide in position with respect to the modified transverse saw blade and making the desired oblique cut.

FIG. 10 is an elevation view of the osteotomy guide of FIG. 1B and the steps of locking the osteotomy guide in position with respect to the removable transverse plate and making the desired oblique cut.

DETAILED DESCRIPTION OF THE PREFERRED EMBODIMENT

Figure 1D:
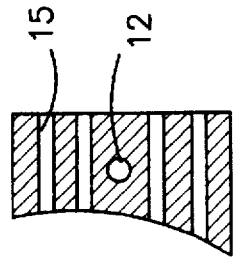
FIG. 1D is a top sectional view of the osteotomy guide of FIG. 1A depicting the guide pin holes.
Figure 1B:
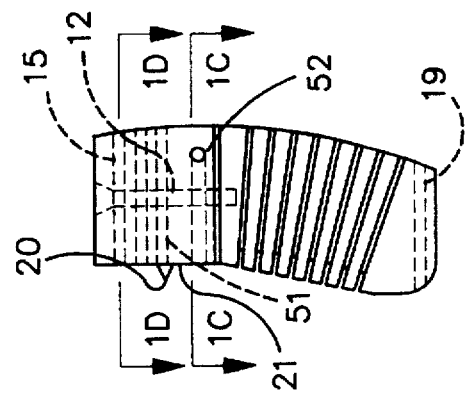
FIG. 1B is a side elevation view of the osteotomy guide of FIG. 1A.

In the drawings many details pertaining to fabrication and maintenance utility well established in the machine construction art and not bearing upon points of novelty are omitted in the interest of descriptive clarity and efficiency. Such details may include threaded connections, lockrings, shear pins, weld lines and the like. The spreading use of electron beam welding eliminates many such features and leaves no visible distinctive lines.

Figure 1C:
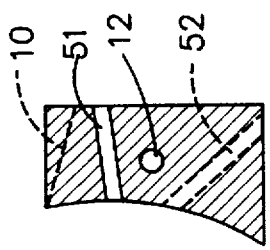
FIG. 1C is a top sectional view of the osteotomy guide of FIG. 1A depicting the angular fixation pin holes.
Figure 1A:
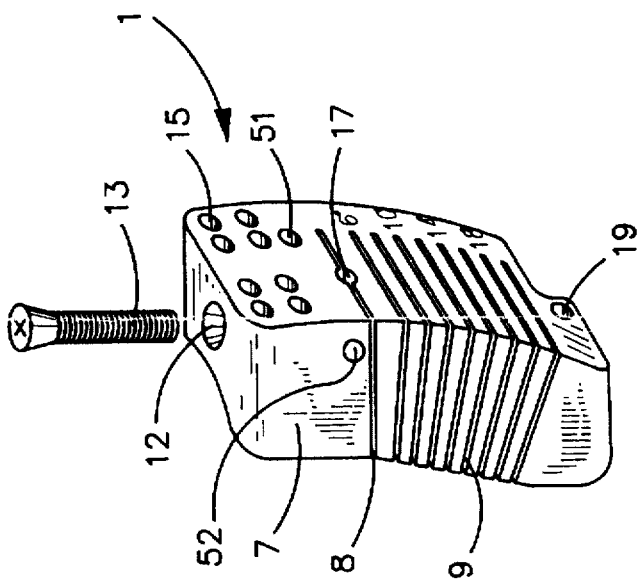
FIG. 1A is a perspective view of a preferred embodiment of the osteotomy guide of the present invention.
Figure 3A:
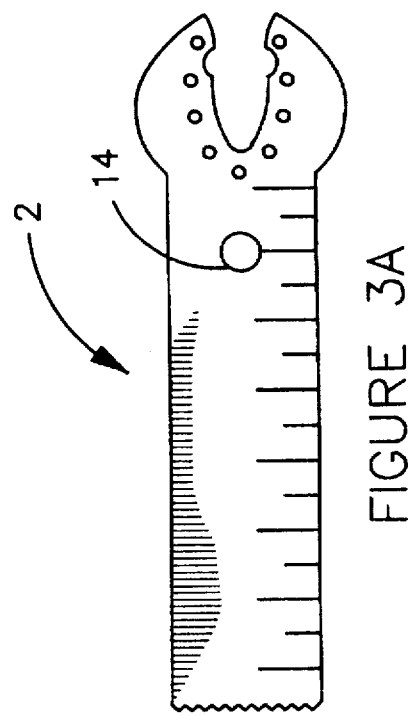
FIG. 3A is a top view of the modified transverse saw blade.

Turning now to FIGS. 1A–1D, an improved tibial osteotomy guide 1 is shown to comprise body 7 into which are formed a single transverse slot 8 and a plurality of oblique guide slots 9. Transverse slot 8 is preferably open on one side of body 7 to accept a saw blade 2 (as shown in FIG. 3A) without damaging the cutting edges on the saw blade 2. In a preferred embodiment, the end wall 10 of transverse slot 8 is slanted away from saw blade 2, as shown in FIG. 1C, in order to reduce the chances of damaging transverse saw blade 2 by reciprocating contact with body 7. Preferably, transverse slot 8 is wide enough in the plane of the transverse cut to accommodate the entire width of transverse saw blade 2, but only slightly larger in height than the thickness thereof. This combination of dimensions for transverse slot 8 minimizes the vertical motion of the blade, provides a stable support for the blade, and enables a very straight transverse cut to be made through the tibia. Transverse slot 8 is formed parallel to the top surface of body 7 and is vertically offset below the top surface by about 20 mm. At least two sharp protrusions 20 are located on the inside face 21 of osteotomy guide 1 which can assist in establishing stable contact between the tibia and the osteotomy guide by superficially penetrating the bone during the placement of pins or during the transverse and oblique cuts.

Figure 8:
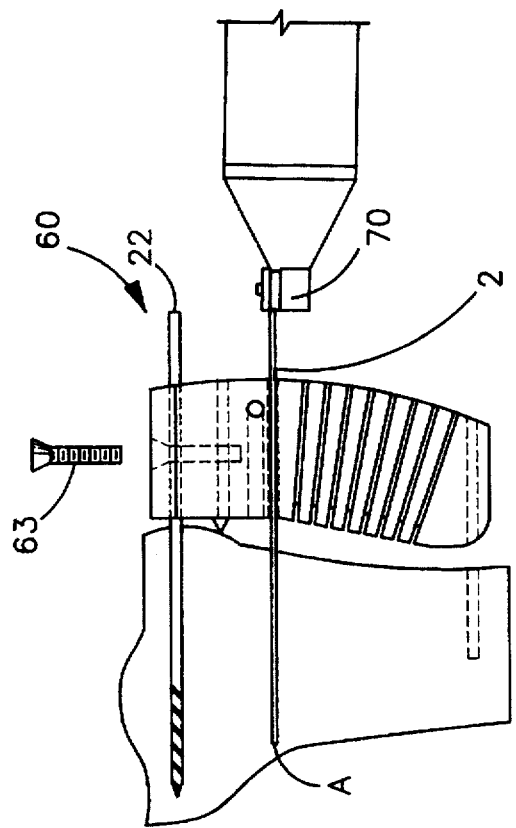
FIG. 8 is an elevation view of the osteotomy guide of FIG. 2B and the step of making the transverse cut.
Figure 7:
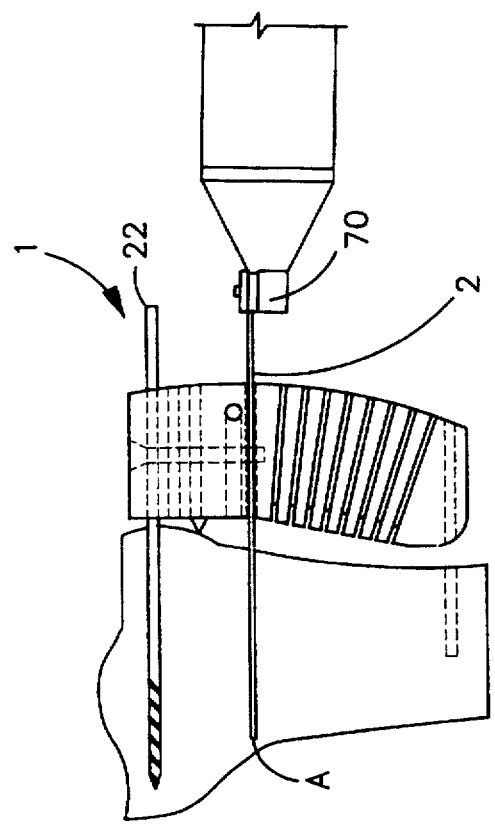
FIG. 7 is an elevation view of the osteotomy guide of FIG. 1B and the step of making the transverse cut.

Preferably, body 7 includes at least eight oblique slots 9 angularly spaced from transverse slot 8 and from one another such that the oblique cutting plane corresponding to each of oblique slots 9 intersects the transverse cutting plane at a predetermined point A, best shown in FIG. 7 and FIG. 8. Oblique slots 9 are spaced about two degrees (2°) apart and allow for six degrees (6°) to twenty degrees (20°) of bone material to be removed. The internal dimensions of each oblique slot 9, including the presence of slanted end walls, are completely analogous to the dimensions of transverse slot 8, although such dimensions are to be considered with respect to the plane of the particular oblique cut to which each oblique slot 9 corresponds. The removal of bone wedges 26 within the 6°–20° range corresponds directly to the degree of correction desired by the surgeon. For tibial osteotomies which are performed on the left knee from a lateral direction, it is preferred that both the transverse slot 8 and the oblique slots 9 open toward the left side of the osteotomy guide 1. Likewise, for those osteotomies which are performed on the right knee from a lateral direction, the transverse and oblique slots 8,9, respectively, should be open toward the right side of the osteotomy guide 1.

A plurality of guide holes 15 arranged in two or more rows spaced vertically apart are also formed through the upper portion of body 7 in planes which are substantially parallel to and above transverse slot 8. The upper row of guide holes 15 would typically be used for the average sized tibia, whereas the lower rows of guide holes 15 would typically be used in osteotomies for smaller tibias. Similarly, the presence of several guide holes 15 on each row permits the surgeon to place pins 22 widely apart or close together, depending upon the size of the tibia. It is expected that most surgeons will prefer to use a pair of pins 22 placed into guide holes 15 on the same row. However, one of ordinary skill will appreciate that any pair of guide holes 15 may be used, regardless of whether they are on the same row or on different rows, as long as the osteotomy guide 1 is fixed along two axes and allowed to slide along the pins 22. Thus, guide holes 15 initially serve as guides for pins 22 placed into the proximal tibia, but also serve as the means for holding and stabilizing the osteotomy guide 1 on the pins 22 once they are in place.

Measurement guide hole 17 is formed into body 7 parallel to guide holes 15 and in the same plane as transverse slot 8. Measurement guide hole 17 is in the same plane as transverse slot 8 so that the precise measurement of tibial depth at the transverse cut level may be made. As will be further explained herein, a drill bit or pin 22 having dimensional markings along its length can be used within measurement guide hole 17 to determine the tibial depth. Finally, reference guide hole 19 is formed into the bottom portion of body 7 so that an additional pin 22 can be guided into the tibia for extra stability or for a reference point. The reference hole created in the tibia is also very useful in realigning the osteotomy guide 1 in the event that additional bone must be removed from the tibia when greater correction is desired.

In order for the transverse and oblique cuts to intersect at their distal extremes, e.g. point A shown in FIGS. 7–11, it is essential that there be a fixed length between body 7 and the distal extreme of the transverse cut. The present invention accomplishes this by at least three methods which can be used alternatively or in conjunction with one another as described below.

Figure 3B:
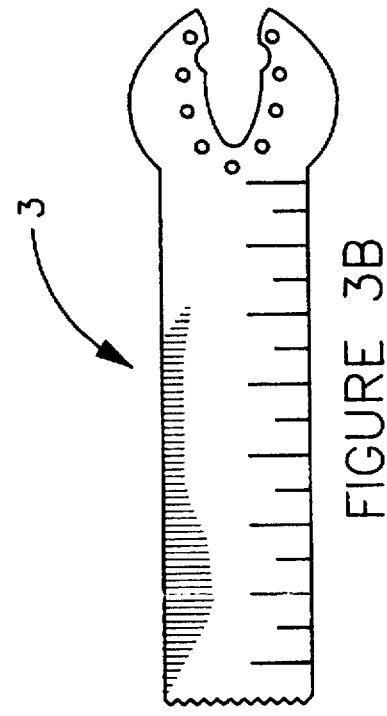
FIG. 3B is a top view of a standard saw blade.

First, the osteotomy guide 1 includes a threaded or non-threaded hole 12, preferably counterbored or countersunk, formed into the top of body 7 and perpendicularly through transverse slot 8 into which a corresponding pin or screw 13 may be inserted. Screw 13 is also matable with a corresponding hole 14 formed into a specially designed transverse saw blade 2, shown in FIG. 3A, when the saw blade 2 is located within transverse slot 8. Transverse saw blade 2 is identical in every respect to saw blades commercially available for such operations, such as saw blade 3 shown in FIG. 3B, except for the presence of the hole 14. Hole 14 should be formed far enough from the cutting edges of transverse saw blade 2 to accommodate the majority of tibial widths seen in practice. If desired, a second transverse saw blade 2 may actually be used to make the oblique cut, because the presence of hole 14 does not affect its cutting ability. This locking feature is explained further herein, and it is also a part of the osteotomy guide disclosed in my previous application Ser. No. 08/384,856. Thus, the osteotomy guide 1 can be retained in a temporarily fixed position with respect to body 7. As an alternative to the hole 14 in transverse saw blade 2, screw 13 may also take the form of a set screw tightened against a predetermined location on saw blade 2. A set screw would not be preferred, however, because it lacks the consistency and predictability of the mating relationship between hole 14 and screw 13.

Figure 4:
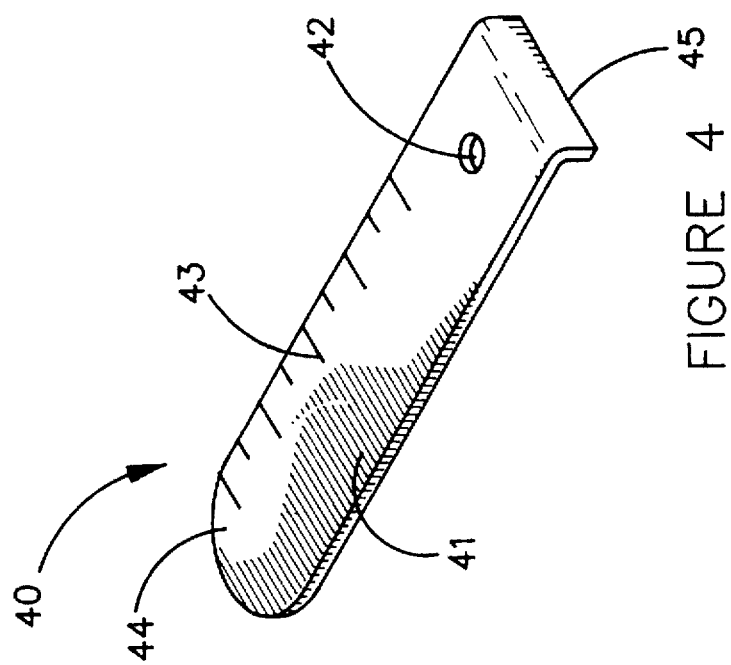
FIG. 4 is a perspective view of the transverse plate which can be used as a substitute for the modified transverse saw blade of FIG. 3A.

An alternative method of fixing the position of the osteotomy guide 1 employs a removable transverse plate 40, shown in FIG. 4, which can be placed into the tibia after the transverse cut. Transverse plate 40 simply comprises a plate member 41 of dimensions comparable to the transverse saw blade 2 and having a locking hole 42 and a series of markings 43 indicating the distance from the distal end 44 of the plate member 41. As in the case of the modified transverse saw blade 2, the location of the locking hole 42 is located at the precise distance from the distal end 44 which will allow for the transverse and oblique cutting planes to meet at the apex A, given the fixed positions of the transverse slot 8 and the oblique slots 9 on the guide 1. Preferably, a small handle 45 is attached to the plate member 41 to facilitate handling during surgery. After the transverse saw blade 2 is withdrawn from the tibia, the transverse plate 40 would be placed into the cut and pushed against the medial bridge 33. Once the transverse plate 40 is in place, the osteotomy guide 1 would be slid back so that screw 13 can lockably engage the guide 1 with the transverse plate 40. With the guide 1 in a fixed relationship to the tibia, the selected oblique cut can then be made. This method of fixation allows the surgeon to use the same saw blade 3 of FIG. 3B for the oblique cut as that used for the transverse cut, resulting in significant cost savings and eliminating saw disassembly and reassembly time.

Finally, an additional method of fixation for the osteotomy guide 1 is available through the use of one or more pins 22 placed through angular fixation holes 51,52. Fixation holes 51,52 are formed through the body 7 of the osteotomy guide 1 in directions that are non-parallel to guide holes 15 and non-parallel to one another. As shown best in the sectional view of FIG. 1C, fixation hole 51 is preferably formed so that a pin 22 can be placed into the tibia from the right side of the guide 1, whereas fixation hole 52 is preferably formed so that a pin 22 can be placed into the tibia from the left side of the guide 1. When a single pin 22 is used in either of fixation holes 51,52, the guide is prevented from sliding along the pins 22 in guide holes 15. If desired, pins 22 may be simultaneously used in both of fixation holes 51,52 for increased stability. If two pins 22 are employed, however, fixation holes 51,52 should be vertically offset from one another to prevent interference between pins 22 placed therein. Of course, the placement of pins 22 through fixation holes 51,52 can be performed to the exclusion of locking the guide 1 onto either the transverse saw blade 2 or the transverse plate 40.

An alternative embodiment 60 of the osteotomy guide of the present invention is also shown in FIGS. 2A–2D. The alternative guide 60 is identical in many respects to the guide 1 described earlier, particularly with respect to the transverse slot 8, the oblique slots 9, the measurement guide hole 17, the angular fixation holes 51,52, and the reference hole 19. It differs primarily in the way the guide 60 is immobilized with respect to the tibia. Specifically, a removable clamp 61 is matingly engageable with the body 7 of the osteotomy guide 60, which can apply pressure against a pair of guide pins 22. A hole 62 is formed through clamp 61 and into body 7 so that a screw 63 can be used to tighten clamp 61 in place using threads tapped into body 7. To ensure alignment between clamp 61 and body 7 and to prevent clamp 61 from free rotation when screw 63 is loosened, a tab 64 is formed on clamp 61 which is matable with a groove 65 formed into body 7. A pair of guide holes 66 are formed along the mating plane between clamp 61 and body 7 such that when clamp 61 is firmly tightened against body 7, the guide pins 22 present within guide holes 66 are gripped by both clamp 61 and body 7. If desired, one or more additional rows of guide holes 66 may also be formed through the osteotomy guide 60. Thus, the osteotomy guide 60 can be easily be moved along guide pins 66 by loosening screw 63, or it can be locked into a precise position with respect to the tibia by tightening screw 63. In order to establish the correct locking distance between the tibia and the guide 60 after the transverse cut, it is preferred that the guide 60 be slid back along the guide pins 22 and along the saw blade 3 still present within the transverse cut until the guide 60 abuts the saw attachment 70. Alternatively, the guide 60 can be slid back along pins 22 until it reaches some marking indicia formed at a predetermined location along saw blade 3. With the guide 60 in position, the clamp 61 may be tightened at the precise location along the guide pins 22 prior to making the oblique cut. It should be stated that in order for this procedure to result in correct positioning of the guide 60, a saw blade 3 having a specific "effective working distance" must be used. The "effective working distance" of a saw blade 3 is the distance from the tip of the saw attachment 70 (or from the marking indicia) to the saw-toothed end of the blade 3. Therefore, the "effective working distance" of the saw blade 3 must correspond to the relative orientation of the transverse slot 8 and oblique slots 9 such that the oblique cut will intersect the transverse cut at the medial bridge 33.

Because the alternative osteotomy guide 60 uses the guide pins 22 and the removable clamp 61 for its primary means for locking the position of the guide 60, there is no need to change the saw blade 3 between the transverse cut and the oblique cut. Also, the angular fixation holes 51,52, whose function has been explained earlier herein, are available as an additional, or alternative, means of securing the guide 60. For additional stabilization, the transverse plate 40 may be inserted within transverse slot 8 and locked with respect to guide 60 using screw 63 if hole 62 is formed to extend across tranverse slot 8, as in the case of FIGS. 1A–1D.

Operation of each of the improved tibial osteotomy guides 1 and 60 is simple and is described with reference to FIGS. 5 through 12. For those steps which apply equally to both osteotomy guides 1 and 60, both reference numerals will be used in those steps. Once the degree of correction is determined through clinical, radiological, and/or mechanical evaluation, the knee joint 31 is exposed by incision as known in the art. A Keith needle, or K-wire 32, is then introduced under the lateral meniscus within the knee joint 31 to identify the joint line. Next, the ostcotomy guide 1,60 is placed against the tibia such that the top surface of the guide 1,60 touches the K-wire 32, and such that it is centered on the lateral plateau in the lateral view. With the osteotomy guide 1,60 in correct vertical and horizontal placement with respect to the joint line, the angular orientation in the lateral view is checked to verify that the transverse slot 8 is parallel to the posterior slope of the knee joint 31.

Figure 5:
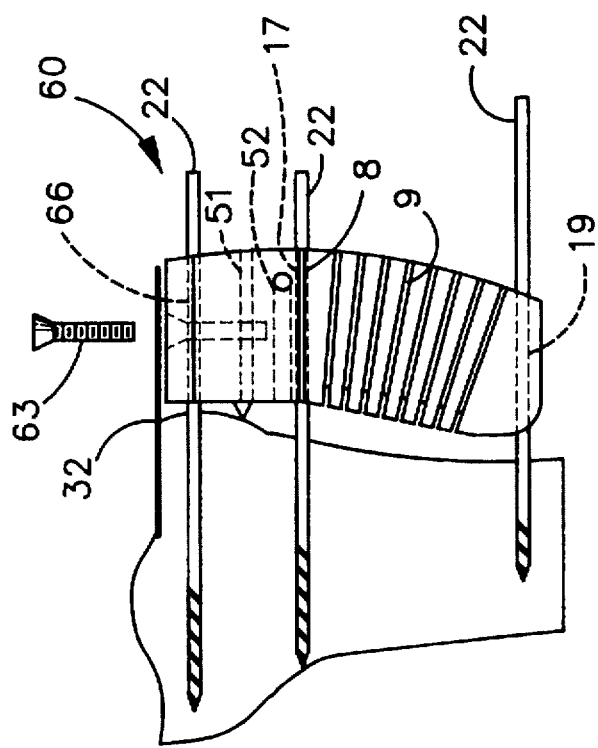
FIG. 5 is an elevation view of the osteotomy guide of FIG. 1B, as well as a tibia with the K-wire inserted and the osteotomy guide supported by the guide pins.
Figure 6:
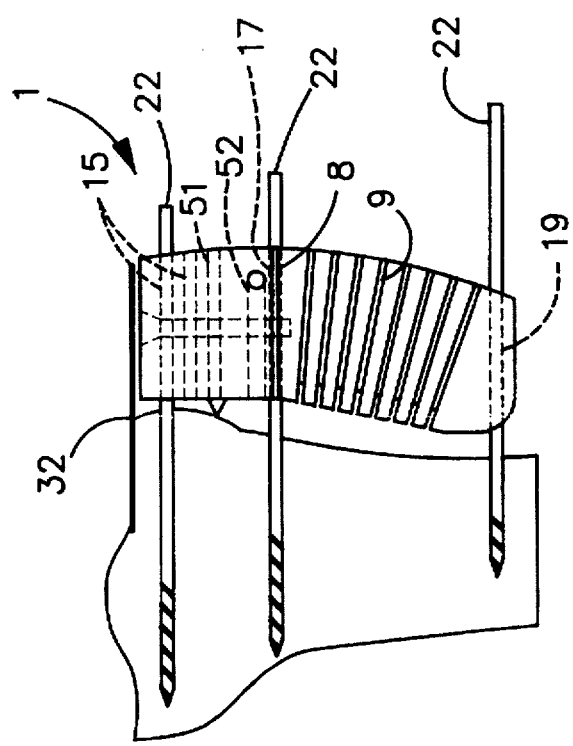
FIG. 6 is an elevation view of the osteotomy guide of FIG. 2B, as well as a tibia with the K-wire inserted and the osteotomy guide supported by the guide pins.

For the first osteotomy guide 1, pins or drill bits 22 are then placed through the top row of guide holes 15 into the proximal tibia parallel to the proximal tibial plateau in the anterior view, as shown in FIG. 5. For smaller tibias, the guide 1 may be removed from the guide pins 22 and replaced onto guide pins 22 through a lower row of holes 15 so that the distance between the transverse cut and the tibial plateau is reduced. For the alternative osteotomy guide 60, the removable clamp 61 is loosened slightly by way of screw 63 only enough so that the pins 22 may slide therethrough, as shown in FIG. 6. Standard fluoroscopic imaging techniques can be employed to verify that the pins 22 are entered in a parallel fashion.

A third pin 22 having dimensional markings inscribed thereon is then drilled through the proximal tibia using the measurement guide hole 17 in body 7. The third pin 22 is advanced through the medial side of the tibia until it begins to protrude from the bone. The depth of the transverse cut can be easily determined by reading the dimensional markings on pin 22 protruding from the outside edge of the guide 1,60 and subtracting the desired width of the roedial bridge 33. Furthermore, the transverse cut depth may also be determined using a depth gauge as disclosed in U.S. Pat. Nos. 5,021,056 and 5,053,039, both issued to Hofmann. Optionally, a reference hole is then created in the cortical bone using either a drill bit or pin 22 guided by the reference guide hole 19, as shown in FIG. 5 or 6. If desired, additional pins 22 may be inserted through angular fixation holes 51,52 and into the tibia for additional stability.

Now that the osteotomy guide 1,60 is stabilized against the tibia, the transverse cut may be made through transverse slot 8, as shown in FIG. 7 in the case osteotomy guide 1, or as shown in FIG. 8 in the case of osteotomy guide 60. The transverse cut can be made with either a standard saw blade 3 having the proper "effective working distance" or the specially designed transverse saw blade 2 shown in FIG. 3A. Regardless of which blade is used, however, the depth of the transverse cut is such that a 5–10 mm roedial bridge 33 (shown in FIGS. 7 and 8) remains intact.

If the modified saw blade 2 of FIG. 3A is used with the osteotomy guide 1, the motorized base of the saw is disengaged after the cut, and the osteotomy guide 1 is slid back along the guide pins 22 until the hole 14 on the transverse saw blade 2 becomes aligned with the hole 12 in body 7. Screw 13 is then inserted through hole 12 to lock the position of the osteotomy guide 1 with respect to the transverse saw blade 2 as in FIG. 9. With the osteotomy guide 1 in the locked position, the oblique slots 9 are now oriented for the oblique cut. If desired, additional pins 22 may be inserted through angular fixation holes 51,52 and into the tibia for additional stability. A standard saw blade 3 is then used to make the selected oblique cut through the oblique slot 9 corresponding to the desired degree of correction. The end of the oblique saw blade 3 should meet the end of transverse saw blade 2 at point A in order to completely cut the wedge of bone 26 to be removed. After the oblique cut is made, the osteotomy guide 1 and transverse saw blade 2 are removed from guide pins 22, and the wedge 26 of bone is removed from the tibia.

If a standard saw blade 3 and the transverse plate 40 are used with the osteotomy guide 1, the transverse cut is made and the saw blade 3 is then withdrawn from the cut. The distal end 44 of the transverse plate 40 is inserted into the transverse slot 8 of the osteotomy guide 1 and advanced into the transverse cut until it makes contact with the roedial bridge 33, as shown in FIG. 10. The plate 40 is then held in place while the osteotomy guide 1 is slid back on the guide pins 22 until the hole 12 in the guide 1 is aligned with the hole 42 in the transverse plate 40. Screw 13 is then inserted into the guide 1 to lock the guide 1 to the transverse plate 40, thereby establishing the proper position of the guide 1 relative to the tibia. If desired, additional pins 22 may be inserted through angular fixation holes 51,52 and into the tibia for additional stability. With the guide 1 in position, the oblique cut can then be made, after which the guide 1 and the transverse plate 40 can be disassembled and the wedge 26 of bone removed.

Figure 11:
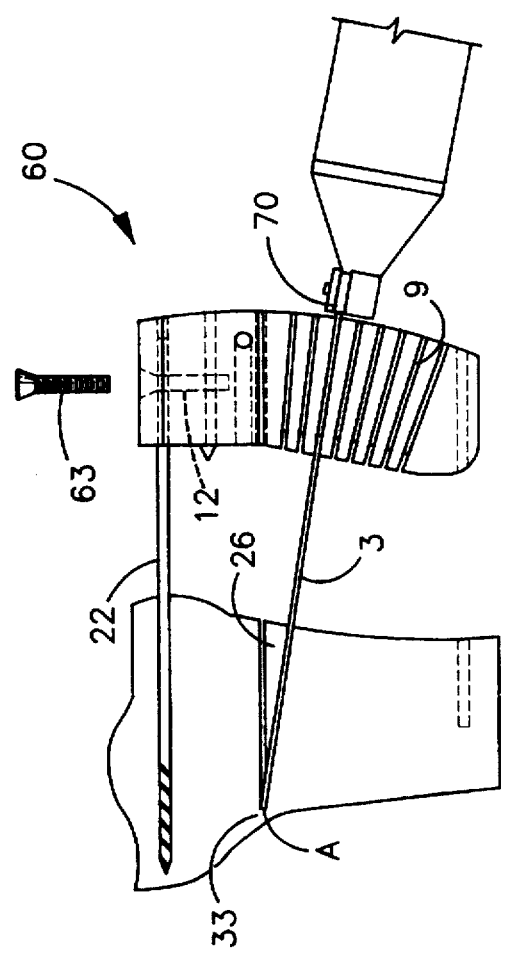
FIG. 11 is an elevation view of the osteotomy guide of FIG. 2B and the steps of locking the osteotomy guide in position with respect to the guide pins and making the desired oblique cut.

In the case of the alternative osteotomy guide 60, there is no advantage to using the modified transverse saw blade 2, because the means for locking the guide 60 does not involve locking contact with the saw blade 2. However, use of such a saw blade 2 would still be possible. Prior to making the oblique cut, the guide 60 is slid back along the guide pins 22 and along the saw blade 3, as shown in FIG. 11, until the guide 60 abuts the saw attachment 70 as explained earlier herein. Screw 63 is then tightened to cause the guide pins 22 to be gripped firmly between clamp 61 and body 7. If desired, additional pins 22 may be inserted through angular fixation holes 51,52 and into the tibia for additional stability. With the guide 60 in position, the oblique cut can then be made by advancing the oblique saw blade 3 until it reaches point A, after which the guide 60 can be disassembled and the wedge 26 of bone removed.

Figure 12:
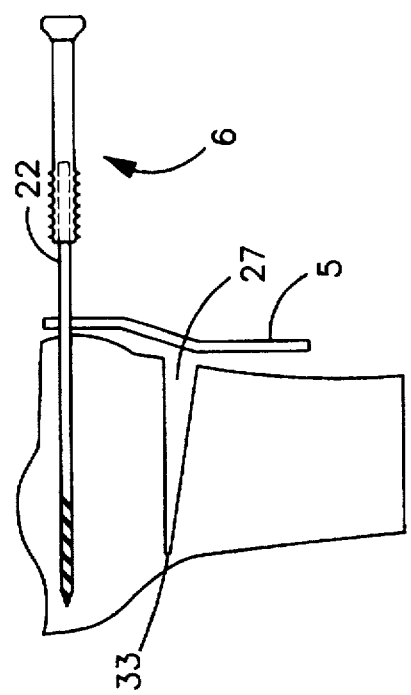
FIG. 12 is an elevation view of the tibia after the osteotomy showing the step of inserting the cannulated screws over the guide pins to secure the L-shaped plate across the osteotomy site.

After removal of the wedge 26 of bone from the wound, the resulting gap 27 is closed in the manner described either in the Hofmann patents or using cannulated screws 6 and an L-plate 5 in the manner described in my previous application Ser. No. 08/384,856, as shown in FIG. 12. Cleaning and closure of the surgical wound are then accomplished through methods known in the art.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

I claim:

1. A surgical kit for performing a tibial osteotomy, comprising:
   (a) an osteotomy guide, comprising:
      (i) mounting means for attaching the guide in a predetermined relation to a tibia;
      (ii) a transverse slot, defining a transverse cutting plane, adapted to receive and guide a transverse cutting blade for making a transverse cut into said tibia; and
      (iii) a plurality of oblique slots angularly offset from said transverse slot, each said oblique slot defining an oblique cutting plane, adapted to receive and guide an oblique cutting blade for making a selected oblique cut into said tibia, wherein the intersection of each of said oblique cutting planes with said transverse cutting plane is adapted to define a wedge of bone which may be removed from said tibia;
   (b) a transverse member adapted to pass through said transverse slot; and
   (c) locking means on said osteotomy guide for lockably engaging said transverse member and positioning said osteotomy guide at a predetermined location relative to said transverse member.

2. The surgical kit of claim 1, wherein said mounting means comprises:
   (a) at least two guide pins for placement into said tibia; and
   (b) at least two rows of guide holes formed into said osteotomy guide adapted to receive said guide pins, wherein said rows are spaced a predetermined vertical distance from one another.

3. The surgical kit of claim 2, wherein said osteotomy guide includes two or more fixation holes each adapted to receive a fixation pin, wherein said fixation holes are formed through said osteotomy guide in directions that are non-parallel to said guide holes.

4. The surgical kit of claim 1, wherein said osteotomy guide includes a measurement guide hole parallel to said transverse cutting plane.

5. The surgical kit of claim 4, wherein said measurement guide hole is in the same plane as said transverse cutting plane.

6. The surgical kit of claim 1, wherein said transverse member comprises a transverse cutting blade.

7. The surgical kit of claim 6, wherein said transverse cutting blade includes a first locking hole formed therethrough; and wherein said locking means on said osteotomy guide includes a second locking hole formed across said transverse slot; and a locking member removably insertable through said first and second locking holes.

8. The surgical kit of claim 1, wherein said transverse member comprises a removable transverse plate having a first locking hole formed therethrough; and wherein said locking means on said osteotomy guide includes a second locking hole formed across said transverse slot; and a locking member removably insertable through said first and second locking holes.

9. The surgical kit of claim 1, wherein the angular offset of said oblique slots from said transverse slot ranges from about six degrees to about twenty degrees.

10. The surgical kit of claim 1, wherein said osteotomy guide further includes a plurality of protrusions sufficient to establish stable contact of said osteotomy guide against the tibia.

11. An osteotomy guide for performing a tibial osteotomy, comprising:
  (a) mounting means for attaching the osteotomy guide in a predetermined relation to a tibia, wherein said mounting means comprises:
    (i) at least two guide pins for placement into said tibia; and
    (ii) at least two rows of guide holes formed into said osteotomy guide adapted to receive said guide pins, wherein said rows are spaced a predetermined vertical distance from one another;
  (b) a transverse slot, defining a transverse cutting plane, adapted to receive and guide a transverse cutting blade for making a transverse cut into said tibia; and
  (c) a plurality of oblique slots angularly offset from said transverse slot, each said oblique slot defining an oblique cutting plane, adapted to receive and guide an oblique cutting blade for making a selected oblique cut into said tibia, wherein the intersection of each of said oblique cutting planes with said transverse cutting plane is adapted to define a wedge of bone which may be removed from said tibia; and
    wherein said transverse slot is between said rows of guide holes and said plurality of said oblique slots.

12. The osteotomy guide of claim 11, further including a measurement guide hole formed parallel to said transverse cutting plane.

13. The osteotomy guide of claim 12, wherein said measurement guide hole is in the same plane as said transverse cutting plane.

14. The osteotomy guide of claim 11, further including two or more fixation holes formed therethrough, each said fixation hole adapted to receive a fixation pin, wherein said fixation holes are formed in directions that are non-parallel to said guide holes.

15. The osteotomy guide of claim 11, wherein the angular offset of said oblique slots from said transverse slot ranges from about six degrees to about twenty degrees.

16. The osteotomy guide of claim 11, further including a plurality of protrusions facing said tibia sufficient to establish stable contact of said osteotomy guide against the tibia.

17. An osteotomy guide for performing a tibial osteotomy, comprising:
  (a) mounting means for attaching the osteotomy guide in a predetermined relation to a tibia, said mounting means comprising at least two guide pins for placement into said tibia, and at least two guide holes formed into said osteotomy guide adapted to receive said guide pins;
  (b) a transverse slot, defining a transverse cutting plane, adapted to receive and guide a transverse cutting blade for making a transverse cut into said tibia;
  (c) a plurality of oblique slots angularly offset from said transverse slot, each said oblique slot defining an oblique cutting plane, adapted to receive and guide an oblique cutting blade for making a selected oblique cut into said tibia, wherein the intersection of each of said oblique cutting planes with said transverse cutting plane is adapted to define a wedge of bone which may be removed from said tibia; and
  (d) locking means on said mounting means for lockably positioning said osteotomy guide at a predetermined location relative to said tibia, said locking means comprising removable clamping means for gripping said guide pins.

18. The osteotomy guide of claim 17, further including a measurement guide hole formed parallel to said transverse cutting plane.

19. The osteotomy guide of claim 18, wherein said measurement guide hole is in the same plane as said transverse cutting plane.

20. The osteotomy guide of claim 17, wherein the angular offset of said oblique slots from said transverse slot ranges from about six degrees to about twenty degrees.

21. The osteotomy guide of claim 17, further including a plurality of protrusions facing said tibia sufficient to establish stable contact of said osteotomy guide against the tibia.

22. An osteotomy guide for performing a tibial osteotomy, comprising:
  (a) mounting means for attaching the osteotomy guide in a predetermined relation to a tibia;
  (b) a transverse slot, defining a transverse cutting plane, adapted to receive and guide a transverse cutting blade for making a transverse cut into said tibia;
  (c) a plurality of oblique slots angularly offset from said transverse slot, each said oblique slot defining an oblique cutting plane, adapted to receive and guide an oblique cutting blade for making a selected oblique cut into said tibia, wherein the intersection of each of said oblique cutting planes with said transverse cutting plane is adapted to define a wedge of bone which may be removed from said tibia; and
  (d) locking means on said osteotomy guide for lockably positioning said osteotomy guide at a predetermined location relative to said tibia, wherein said locking means includes at least two or more fixation holes each adapted to receive a fixation pin, wherein said fixation holes are formed through said osteotomy guide in planes substantially parallel to said transverse slot and in directions that are non-parallel to each other.

23. The osteotomy guide of claim 22, wherein said mounting means includes at least one guide pin for placement into said tibia, and at least one guide hole formed into said osteotomy guide adapted to receive said guide pin.

24. A method of performing a tibial osteotomy, comprising the steps of:
  (a) providing a transverse plate and an osteotomy guide, wherein said osteotomy guide comprises:
    (i) mounting means for attaching the guide in a predetermined relation to a tibia, said tibia having a depth;
    (ii) a transverse slot, defining a transverse cutting plane, adapted to receive and guide a transverse cutting blade;
    (iii) a plurality of oblique slots angularly offset from said transverse slot, each said oblique slot defining an oblique cutting plane, adapted to receive and guide an oblique cutting blade for making a selected oblique cut into said tibia, wherein the intersection of each of said oblique cutting planes with said transverse cutting plane is adapted to define a wedge of bone which may be removed from said tibia; and (iv) locking means for lockably engaging said transverse plate when said transverse plate is in said transverse slot and positioning said osteotomy guide at a predetermined location relative to said transverse plate;

(b) placing said osteotomy guide against said tibia;

(c) extending said transverse cutting blade through said transverse slot;

(d) making a transverse cut through said tibia to a distance less than the depth of said tibia;

(e) extending an oblique cutting blade through one of said plurality of oblique slots;

(f) making an oblique cut through said tibia at an angle intersecting said transverse cut and severing a wedge-shaped portion of said tibia;

(g) removing said wedge-shaped portion to form a void in said tibia, said void being defined by an upper side, created by said transverse cut, and a lower side, created by said oblique cut; and (h) drawing said upper and lower sides of said tibia together and permanently closing said void.

25. The method of claim 24, further comprising the steps of, after making said transverse cut and prior to making said oblique cut:

(a) removing said transverse cutting blade from said transverse slot;

(b) inserting said transverse plate through said transverse slot and across said transverse cut; and (c) locking said osteotomy guide with said locking means against said transverse plate at a predetermined location relative to said transverse plate.

26. A method of performing a tibial osteotomy, comprising the steps of:

(a) providing an osteotomy guide, wherein said osteotomy guide comprises:
  (i) mounting means for attaching the osteotomy guide in a predetermined relation to a tibia, said mounting means comprising at least two guide pins for placement into said tibia, and at least two guide holes formed into said osteotomy guide adapted to receive said guide pins;
  (ii) a transverse slot, defining a transverse cutting plane, adapted to receive and guide a transverse cutting blade for making a transverse cut into said tibia;
  (iii) a plurality of oblique slots angularly offset from said transverse slot, each said oblique slot defining an oblique cutting plane, adapted to receive and guide an oblique cutting blade for making a selected oblique cut into said tibia, wherein the intersection of each of said oblique cutting planes with said transverse cutting plane is adapted to define a wedge of bone for removal from said tibia; and
  (iv) locking means on said mounting means for lockably positioning said osteotomy guide at a predetermined location relative to said tibia, wherein said locking means comprises removable clamping means for gripping said guide pins;

(b) placing said osteotomy guide against said tibia;

(c) extending said transverse cutting blade through said transverse slot;

(d) making a transverse cut through said tibia to a distance less than the depth of said tibia;

(e) locking said osteotomy guide onto said mounting means using said locking means at a predetermined location relative to said tibia;

(f) extending an oblique cutting blade through one of said oblique slots;

(g) making an oblique cut through said tibia at an angle intersecting said transverse cut and severing a wedge-shaped portion of said tibia;

(h) removing said wedge-shaped portion to form a void in said tibia, said void being defined by an upper side, created by said transverse cut, and a lower side, created by said oblique cut; and (i) drawing said upper and lower sides of said tibia together and permanently closing said void.

27. A method of performing a tibial osteotomy, comprising the steps of:

(a) providing an osteotomy guide, wherein said osteotomy guide comprises:
  (i) mounting means for attaching the osteotomy guide in a predetermined relation to a tibia;
  (ii) a transverse slot, defining a transverse cutting plane, adapted to receive and guide a transverse cutting blade for making a transverse cut into said tibia;
  (iii) a plurality of oblique slots angularly offset from said transverse slot, each said oblique slot defining an oblique cutting plane, adapted to receive and guide an oblique cutting blade for making a selected oblique cut into said tibia, wherein the intersection of each of said oblique cutting planes with said transverse cutting plane is adapted to define a wedge of bone for removal from said tibia; and
  (iv) locking means on said osteotomy guide for lockably positioning said osteotomy guide at a predetermined location relative to said tibia, wherein said locking means includes at least two or more fixation holes each adapted to receive a fixation pin, wherein said fixation holes are formed through said osteotomy guide in planes substantially parallel to said transverse slot and in directions that are non-parallel to each other;

(b) placing said osteotomy guide against said tibia;

(c) extending said transverse cutting blade through said transverse slot;

(d) making a transverse cut through said tibia to a distance less than the depth of said tibia;

(e) locking said osteotomy guide at a predetermined location relative to said tibia by inserting said fixation pins through said fixation holes and into said tibia;

(f) extending an oblique cutting blade through one of said oblique slots;

(g) making an oblique cut through said tibia at an angle intersecting said transverse cut and severing a wedge-shaped portion of said tibia;

(h) removing said wedge-shaped portion to form a void in said tibia, said void being defined by an upper side, created by said transverse cut, and a lower side, created by said oblique cut; and (i) drawing said upper and lower sides of said tibia together and permanently closing said void.

\* \* \* \* \*